United States Patent [19]

Treace

[11] 3,953,896
[45] May 4, 1976

[54] PROSTHETIC LIGAMENT
[75] Inventor: James T. Treace, Malibu, Calif.
[73] Assignee: Richards Manufacturing Company, Inc., Memphis, Tenn.
[22] Filed: Sept. 6, 1974
[21] Appl. No.: 503,990

[52] U.S. Cl. .......................................... 3/1; 3/1.9; 128/92 C; 128/92 B
[51] Int. Cl.[2] .......................................... A61F 1/24
[58] Field of Search .......................... 3/1, 1.9–1.911, 3/29, 33–35; 128/92 C, 92 R, 92 B, 92 D

[56] References Cited
UNITED STATES PATENTS

| | | | |
|---|---|---|---|
| 3,513,484 | 5/1970 | Hausner | 3/1 |
| 3,896,500 | 7/1975 | Rambert et al. | 3/1 |
| R1,724 | 7/1864 | Bly | 3/29 |

FOREIGN PATENTS OR APPLICATIONS

| | | | |
|---|---|---|---|
| 834,884 | 3/1952 | Germany | 3/32 |

Primary Examiner—Ronald L. Frinks
Attorney, Agent, or Firm—John R. Walker, III

[57] ABSTRACT

A prosthetic ligament for replacing a natural ligament flexibly connecting two skeletal members together. The prosthetic ligament includes a bridge member made of biocompatible material for joining the two skeletal members together. The bridge member includes a first end portion for fixed attachment to one of the skeletal members, a second end portion for fixed attachment to the other skeletal member, and a central portion for flexibly joining the first and second end portions together. The prosthetic ligament includes first and second nut members for coacting with the first and second end portions of the bridge member to secure the bridge member to the skeletal members. The prosthetic ligament also includes first and second sleeve members positioned adjacent the skeletal members for protecting the bridge member from abrasion as the skeletal members flex relative to each other.

16 Claims, 4 Drawing Figures

PROSTHETIC LIGAMENT

BACKGROUND OF THE INVENTION

1. Field of the Invention

This invention relates generally to prostheses and more specifically to prosthetic ligaments.

2. Description of the Prior Art

Applicant is aware of the U.S. Patent to Tascon-Alonso et al. (U.S. Pat. No. 3,805,300) which discloses a tendon prosthesis that provides union between a damaged tendon and the prosthesis. However, the Tascon-Alonso patent does not disclose or suggest applicant's invention.

Ligaments flexibly connecting skeletal members together are subject to a lot of force and are frequently damaged by being torn apart or the like. When they are so damaged, the ligaments rarely mend satisfactorily. There have been various attempts to correct damaged ligaments. However, heresofar no attempt has been completely satisfactory.

One such attempt has been to surgically mend torn ligaments by sewing the ends of the torn ligament together. This attempt has not been entirely satisfactory because a ligament so repaired does not afford the stability afforded by a healthy ligament and allows the skeletal members held together by the ligament to move in directions not normally allowed, causing pain and undue wear of the skeletal members.

Another attempt to repair the damaged ligament has been to replace the damaged ligament with other body tissue such as muscle or the like. The problem in this attempt is that when muscle or the like is used as a ligament, it will tear in a short period of time. This is because a body typically has only one tissue that will perform as well as and serve the function of any specific ligament and that is the ligament itself.

Other attempts to correct damaged ligaments have been to replace the ligaments with artificial ligaments. More specifically, attempts have been made to replace a damaged natural ligament with suture material or wire. Such artificial ligaments are disadvantageous in that, among other reasons, they do not provide the stability and flexibility of the natural ligament.

SUMMARY OF THE INVENTION

The present invention is directed towards providing a prosthetic ligament that overcomes the problems and disadvantages of prior attempts to correct damaged ligaments. The concept of the present invention is to provide a long lasting prosthetic ligament that allows two natural skeletal members to be securely connected together with substantially the same stability and flexibility as when connected by a healthy natural ligament.

The prosthetic ligament of the present invention includes bridge means for joining first and second skeletal members together. This bridge means includes a flexible central portion for allowing flexure of the first and second skeletal members relative to one another. The prosthetic ligament includes keeper means for securing the bridge means to the first and second skeletal members thereby connecting the first and second skeletal members together and includes bushing means positioned adjacent the first and second skeletal members for protecting the bridge means from abrasion as the first and second skeletal members flex relative to each other.

DESCRIPTION OF THE PREFERRED EMBODIMENT

Figure 1:
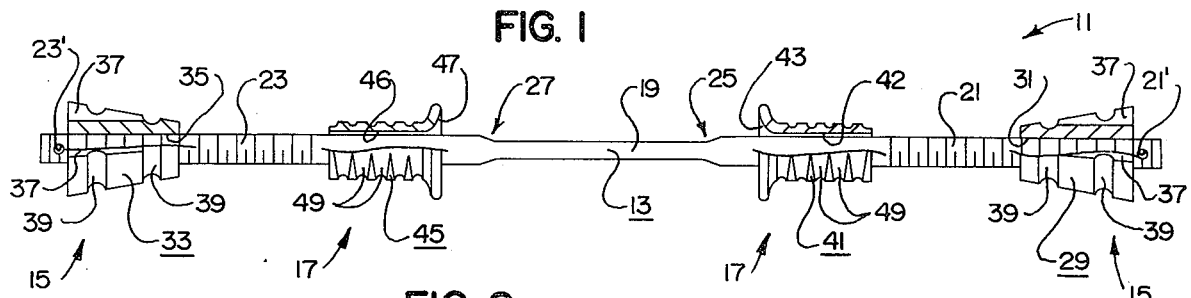
FIG. 1 is a front elevational view of a first embodiment of the prosthetic ligament of the present invention, with portions broken away and sectionalized for purposes of illustration.
Figure 3:
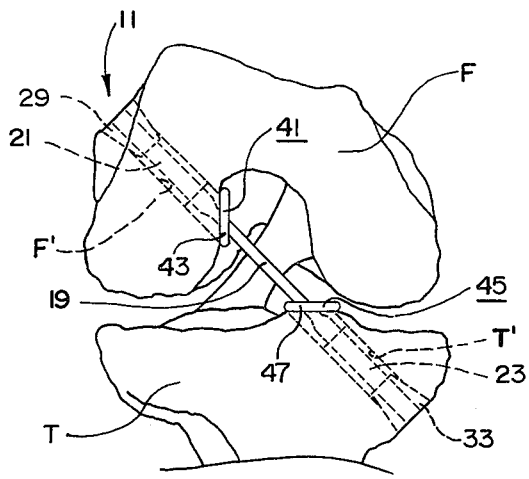
FIG. 3 is a somewhat diagrammatic view of the first embodiment of the prosthetic ligament shown connecting two skeletal members together.
Figure 4:
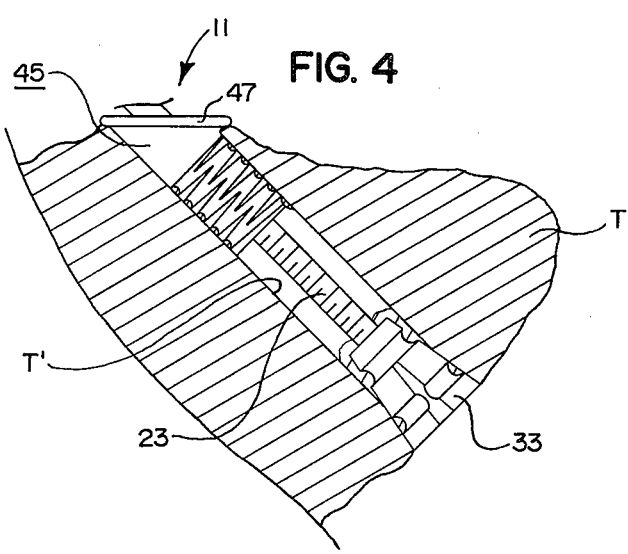
FIG. 4 is an enlarged view of a portion of FIG. 3 showing some parts in section for clarity.

The prosthetic ligament of the present invention is adapted to replace a natural ligament which flexibly connects natural skeletal members together when the natural ligament is damaged beyond repair. A first embodiment of the present invention is shown in FIGS. 1, 3 and 4 of the drawings. In general, the prosthetic ligamenet 11 of the first embodiment includes a bridge means 13, preferably circular in cross-section, for joining first and second skeletal members together; keeper means 15 for securing the bridge means 13 to the first and second skeletal members thereby connecting the first and second skeletal members together; and bushing means 17 positioned adjacent the first and second skeletal members for protecting the bridge means 13 from abrasion as the first and second skeletal members flex relative to each other.

The bridge means 13 is made of a suitable biocompatible material, preferably ultrahigh molecular weight polyethylene. The bridge means 13 includes a flexible elongated central portion 19 for allowing flexure of the first and second skeletal members relative to one another. Preferably, the bridge means 13 includes a threaded shaft-like first end portion 21 for passing through an aperture in the first skeletal member and a threaded shaft-like second end portion 23 for passing through an aperture in the second skeletal member. The central portion 19 is preferably integral with the first and second end portions 21, 23 thereby joining the first and second end portions 21, 23 together. The cross-sectional area of the central portion 19 is preferably smaller than the cross-sectional area of the first and second end portions 21, 23 to allow proper flexure of the central portion 19 as the first and second skeletal members flex relative to one another. Preferably, the bridge means 13 includes a first reducing portion 25, which is preferably frustro-conical, intermediate the central portion 19 and the first end portion 21 to allow gradual reduction of the cross-sectional area of the bridge means 13 between the central portion 19 and the first end portion 21 to prevent stress buildup at the junction between the central portion 19 and the first end portion 21 as the central portion 19 flexes. Likewise, the bridge means 13 includes a second reducing portion 27 intermediate the central portion 19 and the second end portion 23 to allow gradual reduction of the cross-sectional area of the bridge means 13 between the central portion 19 and the second end portion 23 to prevent stress buildup at the junction between the central portion 19 and the second end portion 23 as the central portion 19 flexes.

The keeper means 15 preferably includes a first fastening member such as a first nut member 29 having a threaded aperture 31 for coacting with the first end portion 21 of the bridge means 13 to secure the first end portion 21 of the bridge means 13 to the first skeletal member. Likewise, the keeper means 15 preferably includes a second fastening member such as a second nut member 33 having a threaded aperture 35 for coacting with the second end portion 25 of the bridge means 13 to secure the second end portion 25 of the bridge means 13 to the second skeletal member. The first and second nut members 29, 33 are formed of a suitable biocompatible material, preferably an ultra-high molecular weight polyethylene. Each of the first and second nut members 29, 33 is preferably provided with grip portions 37 for allowing the first and second nut members 29, 31 to be properly screwed onto the first and second end portions 21, 23 of the bridge means 13. More specifically, the grip portions 37 allow a wrench or the like to coact with the first and second nut members 29, 33 to screw the first and second nut members 29, 33 onto the first and second end portions 21, 23 of the bridge means 13. Each of the first and second nut members 29, 33 preferably includes fixation means such as grooves 39 in the outer surface of the first and second nut members 29, 33 for coacting with typical bone cement to fixedly secure the first and second nut members 29, 33 in the apertures in the first and second skeletal members.

The bushing means 17 includes a first sleeve member 41 having a longitudinal aperture 42 with a flared mouth portion 43 for positioning adjacent the aperture in the first skeletal member with the flared mouth portion 43 directed towards the second skeletal member to allow the first end portion 21 of the bridge means 13 to pass therethrough. The bushing means 17 also includes a second sleeve member 45 having a longitudinal aperture 46 with a flared mouth portion 47 for positioning adjacent the aperture in the second skeletal member with the flared mouth portion directed toward the first skeletal member to allow the second end portion 23 of the bridge means 13 to pass therethrough. The first and second sleeve members 41, 45 are formed of a suitable biocompatible material, preferably stainless steel. Each of the first and second sleeve members 41, 45 include fixation means such as grooves 49 in the outer surface thereof positioned substantially transverse to the axis of the apertures 42, 46 therethrough for coacting with typical bone cement to fixedly position the first and second sleeve members 41, 45 adjacent the apertures in the first and second skeletal members. Such grooves 49 may be provided by double threading each of the sleeve members 41, 45 in opposite directions. The apertures 42, 46 through the first and second sleeve members 41, 45 are preferably slightly larger in cross-sectional area than the bridge means 13 so that the bridge means 13 is free to move in the first and second sleeve members 41, 45. The flared mouth portions 43, 47 of the first and second sleeve members 41, 45 may be positioned at right angles to the longitudinal axis of the apertures 42, 46 through the first and second sleeve members 41, 45, as shown in FIGS. 1 and 2, or, if desired, may be at any angle relative thereto depending on the angle of the surface of the skeletal members for allowing the flared mouth portions 43, 47 to lie in the same plane as the outer surface of the skeletal members, as shown in FIGS. 3 and 4.

Although the prosthetic ligament 11 of the present invention can be used to replace substantially any ligament flexibly connecting two skeletal members together, it is especially adapted for use in replacing the cruciate ligament flexibly connecting the femur and tibia together in a knee joint. Thus, the insertion of the prosthetic ligament 11 will be explained with respect to replacing a damaged cruciate ligament, but it should be understood that a similar procedure would be used to replace substantially any ligament flexibly connecting two skeletal members together.

When it is desired to replace a natural cruciate ligament with the prosthetic ligament 11 of the present invention, an incision is made in the knee to expose the joint between the femur F and the tibia T in a manner well known to those skilled in the art (see FIG. 3). Next, the points of attachment of the natural cruciate ligament to the femur F and tibia T are located. Preferably, a guide pin is then run through the femur F and tibia T starting at the points of attachment of the cruciate ligament thereto. Then, a cannulated drill is passed through the femur F and tibia T along the guide pins to form apertures or holes F', T' therein. The first sleeve member 41 is then inserted into the hole F' in the femur F and fixedly secured therein with aid of bone cement. Likewise, the second sleeve member 45 is inserted into the hole T' in the tibia T and fixedly secured therein with the aid of bone cement. Next, the bridge means 13 is inserted through the holes F', T' in the femur F and tibia T. Preferably, the first and second end portions 21, 23 are provided with transverse apertures 21', 23' for allowing a length of suture material to be passed therethrough to aid in positioning the bridge means 13 in the holes F', T'. Care is taken to make sure that only the central portion 19 of the bridge means 13 is in the joint space between the femur F and the tibia T. In this regard, since the joint space between the femur F and the tibia T varies among people, the central portion 19 of the prosthetic ligament 11 of the present invention will be provided with a variety of different lengths to accommodate various joint spaces. Next, bone cement is placed in the outer ends of the holes F', T' in the femur F and tibia T to secure the outer ends of the first and second end portions 21, 23 of the bridge means 13 therein. The first and second nut members 29, 33 are then screwed on the first and second end portions 21, 23 of the bridge means 13 and tightened with a wrench or the like to place the bridge means 13 in proper tension. Preferably, bone cement is provided in the threaded apertures 31, 35 of the first and second nut members 29, 33 to aid in fixedly attaching the first and second nut members 29, 33 to the bridge means 13, femur F, and tibia T. Next, the outer ends of the bridge means 13 are cut off to prevent them from protruding through the skin after the incision is closed. Finally, the incision is closed in a manner well known to those skilled in the art.

Figure 2:
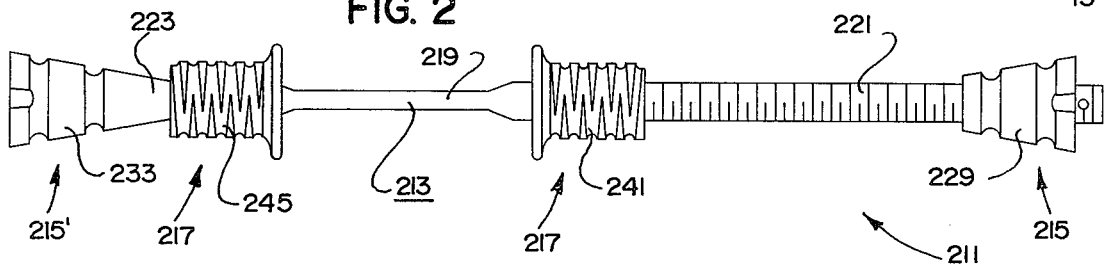
FIG. 2 is a front elevational view of a second embodiment of the prosthetic ligament of the present invention.

A second embodiment of the present invention is shown in FIG. 2 of the drawings. In this second embodiment, the prosthetic ligament 211 includes a bridge means 213 having a central portion 219 and a threaded shaft-like first end portion 221 identical to the central portion 19 and first end portion 21 of the first embodiment; a keeper means 215 having a first fastening member such as a first nut member 229 identical to the first nut member 29 of the first embodiment; and a bushing means 217 having first and second sleeve means 241, 245 identical with the first and second sleeve means 41, 45 of the first embodiment. In this second embodiment, the prosthetic ligament 211 includes a second end portion 223 and a second fastening member 233 made integral with one another to provide keeper means 215' having an exterior surface similar to the exterior of keeper means 15. In this embodiment, to replace a ligament with the prosthetic ligament 211, the first end portion 221 of the bridge means 213 is passed through the aperture in the second skeletal member, past the joint space between the first and second skeletal members, and into the aperture in the first skeletal member where the first nut member 229 is screwed onto the first end portion 221 to secure the bridge means 213 to the first and second skeletal members thereby flexibly connecting the first and second skeletal members together.

As thus constructed and inserted, the present invention provides a prosthetic ligament that allows two skeletal members to be securely connected together with substantially the same stability and flexibility as when connected by a healthy natural ligament. In addition, the prosthetic ligament of the present invention will withstand a lot of force and flexure without damage or failure. In this regard, the reducing portions and the flared bushings play an important part.

Although the invention has been described and illustrated with respect to preferred embodiments thereof, it is not to be so limited since changes and modifications may be made therein which are within the full intended scope of the invention.

I claim:

1. A prosthetic ligament for replacing a natural ligament flexibly connecting first and second natural skeletal members together, said prosthetic ligament comprising:
    a. bridge means for joining the first and second skeletal members together, said bridge means including a first end portion for being secured to the first skeletal member and including a second end portion for being secured to the second skeletal member, said bridge means including a flexible central portion for allowing flexure of the first and second skeletal members relative to one another;
    b. keeper means for securing said bridge means to the first and second skeletal members thereby connecting the first and second skeletal members together, said keeper means including a first fastening member for securing said first end portion of said bridge means to the first skeletal member and including a second fastening member for securing said second end portion of said bridge means to the second skeletal member, at least said first fastening member being adjustable in a direction longitudinally of said bridge means, and
    c. bushing means for positioning adjacent the first and second skeletal members to protect said bridge means from abrasion as the first and second skeletal members flex relative to each other.

2. The prosthetic ligament of claim 1 in which said bridge means includes a threaded first end portion for passing through an aperture in the first skeletal member and includes a threaded second end portion for passing through an aperture in the second skeletal member, and in which said keeper means includes a first nut member having a threaded aperture for coacting with said first end portion of said bridge means to secure said first end portion of said bridge means to the first skeletal member and includes a second nut member having a threaded aperture for coacting with said second end portion of said bridge means to secure said second end portion of said bridge means to the second skeletal member.

3. The prosthetic ligament of claim 2 in which said central portion of said bridge means joins said first and second end portions of said bridge means together and in which said central portion is smaller in cross-sectional area than said first and second end portions for allowing proper flexure of said central portion to permit the first and second skeletal members to flex relative to each other.

4. A prosthetic ligament for replacing a natural ligament flexibly connecting first and second natural skeletal members together, said prosthetic ligament comprising:
    a. bridge means for joining the first and second skeletal members together, said bridge means including a first end portion for being secured to the first skeletal member and including a second end portion for being secured to the second skeletal member, said bridge means including a flexible central portion for allowing flexure of the first and second skeletal members relative to one another, said central portion of said bridge means being of reduced cross-sectional area, said bridge means including first and second reducing portions respectively joining said first and second end portions with said central portion; and
    b. keeper means for securing said bridge means to the first and second skeletal members thereby connecting the first and second skeletal members together, said keeper means including a first fastening member for securing said first end portion of said bridge means to the first skeletal member and including a second fastening member for securing said second end portion of said bridge means to the second skeletal member, at least said first fastening member being adjustable in a direction longitudinally of said bridge means.

5. The prosthetic ligament of claim 4 in which each of said reducing portions is frustro-conical.

6. A prosthetic ligament for replacing a natural ligament flexibly connecting first and second skeletal members together, said prosthetic ligament comprising:
    a. bridge means for joining the first and second skeletal members together, said bridge means including a flexible central portion for allowing flexure of the first and second skeletal members relative to one another, said bridge means including a first end portion for passing through an aperture in the first skeletal member and including a second end portion for passing through an aperture in the second skeletal member;
    b. keeper means for securing said bridge means to the first and second skeletal members thereby connecting the first and second skeletal members together; and
    c. bushing means for positioning adjacent the first and second skeletal members to protect said bridge means from abrasion as the first and second skeletal members flex relative to each other, said bushing means including a first sleeve member having a longitudinal aperture for positioning adjacent the aperture in the first skeletal member to allow said first end portion of said bridge means to pass therethrough and including a second sleeve member having a longitudinal aperture for positioning adjacent the aperture in the second skeletal member to allow said second end portion of said bridge means to pass therethrough.

7. A prosthetic ligament for replacing a natural ligament flexibly connecting first and second skeletal members together, said prosthetic ligament comprising:
   a. bridge means for joining the first and second skeletal members together, said bridge means including a flexible central portion for allowing flexure of the first and second skeletal members relative to one another, said bridge means including a first end portion for passing through an aperture in the first skeletal member and including a second end portion for passing through an aperture in the second skeletal member;
   b. keeper means for securing said bridge means to the first and second skeletal members thereby connecting the first and second skeletal members together, said keeper means including a first member for coacting with said first end portion of said bridge means to secure said first end portion of said bridge means to the first skeletal member and including a second member for coacting with said second end portion of said bridge means to secure said second end portion of said bridge means to the second member; and
   c. bushing means for positioning adjacent the first and second skeletal members to protect said bridge means from abrasion as the first and second skeletal members flex relative to each other, said bushing means including a first sleeve member having a longitudinal aperture for positioning adjacent the aperture in the first skeletal member to allow said first end portion of said bridge means to pass therethrough and including a second sleeve member having a longitudinal aperture for positioning adjacent the aperture in the second skeletal member to allow said second end portion of said bridge means to pass therethrough.

8. A prosthetic ligament for replacing a natural ligament flexibly connecting first and second skeletal members together, said prosthetic ligament comprising:
   a. bridge means for joining the first and second skeletal members together, said bridge means including a flexible central portion for allowing flexure of the first and second skeletal members relative to one another, said bridge means including a threaded first end portion for passing through an aperture in the first skeletal member and including a threaded second end portion for passing through an aperture in the second skeletal member, said central portion of said bridge means joining said first and second end portions of said bridge means together, said central portion being smaller in cross-sectional area than said first and second end portions for allowing proper flexure of said central portion to permit the first and second skeletal members to flex relative to each other, said bridge means including first and second reducing portions intermediate said first and second end portions and said central portion for allowing gradual reduction of the cross-sectional area of said bridge means to prevent stress build-up at the junction between said first and second end portions and said central portion as said central portion flexes;
   b. keeper means for securing said bridge means to the first and second skeletal members thereby connecting the first and second skeletal members together, said keeper means including a first nut member having a threaded aperture for coacting with said first end portion of said bridge means to secure said first end portion of said bridge means to the first skeletal member and including a second nut member having a threaded aperture for coacting with said second end portion of said bridge means to secure said second end portion of said bridge means to the second skeletal member; and
   c. bushing means for positioning adjacent the first and second skeletal members to protect said bridge means from abrasion as the first and second skeletal members flex relative to each other.

9. The prosthetic ligament of claim 8 in which said bridge means and said keeper means are composed of a flexible biocompatible plastic.

10. A prosthetic ligament for replacing a natural ligament flexibly connecting first and second skeletal members together, said prosthetic ligament comprising:
    a. bridge means for joining the first and second skeletal members together, said bridge means including a flexible central portion for allowing flexure of the first and second skeletal members relative to one another, said bridge means including a threaded first end portion for passing through an aperture in the first skeletal member and including a threaded second end portion for passing through an aperture in the second skeletal member;
    b. keeper means for securing said bridge means to the first and second skeletal members thereby connecting the first and second skeletal members together, said keeper means including a first nut member having a threaded aperture for coacting with said first end portion of said bridge means to secure said first end portion of said bridge means to the first skeletal member and including a second nut member having a threaded aperture for coacting with said second end portion of said bridge means to secure said second end portion of said bridge means to the second skeletal member; and
    c. bushing means for positioning adjacent the first and second skeletal members to protect said bridge means from abrasion as the first and second skeletal members flex relative to each other, said bushing means including a first sleeve member having a longitudinal aperture for positioning adjacent the aperture in the first skeletal member to allow said first end portion of said bridge means to pass therethrough and including a second sleeve member having a longitudinal aperture for positioning adjacent the aperture in the second skeletal member to allow said second end portion of said bridge means to pass therethrough.

11. The prosthetic ligament of claim 10 in which said first sleeve member of said bushing means includes a first flared mouth portion, in which said second sleeve member of said bushing means includes a second flared mouth portion, in which said first sleeve member of said bushing means is positioned adjacent the aperture in the first skeletal member with said first flared mouth portion directed toward the second skeletal member, and in which said second sleeve member of said bushing means is positioned adjacent the aperture in the second skeletal member with said second flared mouth portion directed toward the first skeletal member.

12. The prosthetic ligament of claim 11 in which each of said first and second sleeve members of said bushing means includes fixation means for coacting with bone cement to fixedly position said first and second sleeve members adjacent the apertures in the first and second skeletal members.

13. The prosthetic ligament of claim 12 in which each of said first and second nut members of said keeper means includes fixation means for coacting with bone cement to fixedly secure said first and second nut members to the first and second skeletal members.

14. A prosthetic cruciate ligament for replacing a natural cruciate ligament flexibly connecting the femur and tibia together in a knee joint, said prosthetic cruciate ligament comprising:
   a. elongated bridge means formed of a biocompatible material for joining the femur and tibia together; said bridge means including a threaded shaft-like first end portion for passing through an aperture in the femur, a threaded shaft-like second end portion for passing through an aperture in the tibia, and a flexible central portion for joining said first and second end portions together and for allowing flexure of the femur and tibia relative to one another, said central portion being smaller in cross-sectional area than said first and second end portions to allow proper flexure of said central portion to permit the femur and tibia to flex relative to one another; said bridge means including first and second reducing portions intermediate said first and second end portions and said central portion for allowing gradual reduction of the cross-sectional area of said bridge means to prevent stress build-up at the junction between said first and second end portions and said central portion as said central portion flexes;
   b. keeper means formed of a biocompatible material for securing said bridge means to the femur and tibia thereby flexibly connecting the femur and tibia together, said keeper means including a first nut member having a threaded aperture for coacting with said first end portion of said bridge means to secure said first end portion of said bridge means to the femur and including a second nut member having a threaded aperture for coacting with said second end portion of said bridge means to secure said second end portion of said bridge means to the tibia, each of a first and second nut members including fixation means for coacting with bone cement to fixedly secure said first and second nut members to the femur and tibia; and
   c. bushing means formed of a biocompatible material for positioning adjacent the femur and tibia to protect said bridge means from abrasion as the femur and tibia flex relative to one another, said bushing means including a first sleeve member having a longitudinal aperture with a flared mouth portion for positioning adjacent the aperture in the femur with said flared mouth portion directed toward the tibia to allow said first end portion of said bridge means to pass therethrough and including a second sleeve member having a longitudinal aperture with a flared mouth portion for positioning adjacent the aperture in the tibia with said flared mouth portion directed toward the femur to allow said second end portion of said bridge means to pass therethrough, each of said first and second sleeve members including fixation means for coacting with bone cement to fixedly position said first and second sleeve members adjacent the apertures in the femur and tibia.

15. A prosthetic ligament for replacing a natural ligament flexibly connecting first and second skeletal members together, said prosthetic ligament comprising:
   a. bridge means for joining the first and second skeletal members together, said bridge means including a flexible central portion for allowing flexure of the first and second skeletal members relative to one another, said bridge means including a first end portion for passing through an aperture in the first skeletal member and including a second end portion for passing through an aperture in the second skeletal member, said central portion of said bridge means joining said first and second end portions of said bridge means together, said central portion being smaller in cross-sectional area than said first and second end portions for allowing proper flexure of said central portion to permit the first and second skeletal members to flex relative to one another, said bridge means including first and second reducing portions intermediate said first and second end portions and said central portion for allowing gradual reduction of the cross-sectional area of said bridge means to prevent stress build-up at the junction between said first and second end portions and said central portion as said central portion flexes; and
   b. keeper means for securing said bridge means to the first and second skeletal members thereby connecting the first and second skeletal members together.

16. A prosthetic ligament for replacing a natural ligament flexibly connecting first and second skeletal members together, said prosthetic ligament comprising:
   a. bridge means for joining the first and second skeletal members together, said bridge means including a flexible central portion for allowing flexure of the first and second skeletal members relative to one another, said bridge means including a first end portion for passing through an aperture in the first skeletal member and including a second end portion for passing through an aperture in the second skeletal member, said central portion of said bridge means joining said first and second end portions of said bridge means together, said central portion being smaller in cross-sectional area than said first and second end portions for allowing proper flexure of said central portion to permit the first and second skeletal members to flex relative to each other, said bridge means including first and second reducing portions intermediate said first and second end portions and central portion for allowing gradual reduction of the cross-sectional area of said bridge means to prevent stress build-up at a junction between said first and second end portions and said central portion as said central portion flexes; and
   b. keeper means for securing said bridge means to the first and second skeletal members thereby connecting the first and second skeletal members together, said keeper means including a first member for coacting with said first end portion of said bridge means to secure said first end portion of said bridge means to the first skeletal member and including a second member for coacting with said second end portion of said bridge means to secure said second end portion of said bridge means to the second skeletal member;

c. bushing means for positioning adjacent the first and second skeletal members to protect said bridge means from abrasion as the first and second skeletal members flex relative to each other.

* * * * *